(12) United States Patent
Venkatraman et al.

(10) Patent No.: US 10,517,605 B2
(45) Date of Patent: Dec. 31, 2019

(54) EMBOLIC DEVICE, AN APPARATUS FOR EMBOLIZING A TARGET VASCULAR SITE AND A METHOD THEREOF

(71) Applicants: Nanyang Technological University, Singapore (SG); Singapore Health Services PTE LTD, Singapore (SG)

(72) Inventors: Subramanian Venkatraman, Singapore (SG); Weimin Huang, Singapore (SG); Yee Shan Wong, Singapore (SG); Abhijit Vijay Salvekar, Singapore (SG); Kiang Hiong Tay, Singapore (SG)

(73) Assignees: Nanyang Technological University, Singapore (SG); Singapore Health Services PTE Ltd, Singapore (SG)

( * ) Notice: Subject to any disclaimer, the term of this patent is extended or adjusted under 35 U.S.C. 154(b) by 495 days.

(21) Appl. No.: 15/110,328

(22) PCT Filed: Jan. 8, 2015

(86) PCT No.: PCT/SG2015/000002
§ 371 (c)(1),
(2) Date: Jul. 7, 2016

(87) PCT Pub. No.: WO2015/105459
PCT Pub. Date: Jul. 16, 2015

(65) Prior Publication Data
US 2016/0331380 A1    Nov. 17, 2016

Related U.S. Application Data

(60) Provisional application No. 61/925,983, filed on Jan. 10, 2014.

(51) Int. Cl.
*A61B 17/12* (2006.01)
*A61B 90/00* (2016.01)
*A61B 17/00* (2006.01)

(52) U.S. Cl.
CPC .... *A61B 17/12145* (2013.01); *A61B 17/1204* (2013.01); *A61B 17/1219* (2013.01);
(Continued)

(58) Field of Classification Search
CPC .......... A61B 17/12145; A61B 17/1204; A61B 90/39; A61B 17/12109; A61B 17/1219;
(Continued)

(56) References Cited

U.S. PATENT DOCUMENTS 6,550,480 B2   4/2003   Feldman et al.
8,951,283 B2 * 2/2015   Khosravi ......... A61B 17/00491
                                                606/213

(Continued)

FOREIGN PATENT DOCUMENTS

WO    2007/006139 A1   1/2007

OTHER PUBLICATIONS

European Search Report from European Patent Application No. 15 735 449.9 dated Aug. 14, 2017.
(Continued)

*Primary Examiner* — Katherine M Shi
*Assistant Examiner* — Michael G Mendoza
(74) *Attorney, Agent, or Firm* — Patterson + Sheridan, LLP

(57) ABSTRACT

According to embodiments of the present invention, an embolic device for embolizing a target vascular site is provided. The embolic device includes a biodegradable shape memory element having an original shape and a deformed shape, wherein the biodegradable shape memory element in the deformed shape is in at least one dimension
(Continued)

of a smaller size than the biodegradable shape memory element in the original shape, and wherein the biodegradable shape memory element is provided in the deformed shape and configured to resume the original shape in response to an external stimulus being applied to the biodegradable shape memory element in its deformed shape, to embolize the target vascular site and prevent fluid flow through the target vascular site. According to further embodiments of the present invention, an apparatus for embolizing a target vascular site and a method thereof are also provided.

12 Claims, 10 Drawing Sheets

(52) U.S. Cl.
CPC .. *A61B 17/12031* (2013.01); *A61B 17/12109* (2013.01); *A61B 17/12181* (2013.01); *A61B 90/39* (2016.02); *A61B 2017/00004* (2013.01); *A61B 2017/00871* (2013.01); *A61B 2017/00893* (2013.01); *A61B 2017/00898* (2013.01); *A61B 2090/3966* (2016.02)

(58) Field of Classification Search
CPC ........ A61B 17/12181; A61B 17/12031; A61B 2090/3966; A61B 2017/00893; A61B 2017/00898; A61B 2017/00004; A61B 2017/00871

See application file for complete search history.

(56) References Cited

U.S. PATENT DOCUMENTS

| | | | |
|---|---|---|---|
| 2002/0040239 A1* | 4/2002 | Murayama | A61B 17/12022 623/1.34 |
| 2004/0091543 A1 | 5/2004 | Bell et al. | |
| 2005/0075405 A1 | 4/2005 | Wilson et al. | |
| 2006/0116709 A1* | 6/2006 | Sepetka | A61B 17/12022 606/200 |
| 2006/0276831 A1 | 12/2006 | Porter et al. | |
| 2007/0056591 A1* | 3/2007 | McSwain | A61B 17/12022 128/831 |
| 2007/0078480 A1* | 4/2007 | Belenkaya | A61B 17/12022 606/200 |
| 2012/0046687 A1 | 2/2012 | Trommeter et al. | |
| 2012/0192872 A1 | 8/2012 | Rudakov et al. | |

OTHER PUBLICATIONS

Office Action from Chinese Patent Application No. 201580013207.5 dated May 26, 2017.
International Search Report and Written Opinion, PCT/SG2015/000002, dated Aug. 3, 2015.

* cited by examiner

EMBOLIC DEVICE, AN APPARATUS FOR EMBOLIZING A TARGET VASCULAR SITE AND A METHOD THEREOF

CROSS-REFERENCE TO RELATED APPLICATION

This application claims the benefit of priority of U.S. provisional application No. 61/925,983, filed on 10 Jan. 2014, the content of it being hereby incorporated by reference in its entirety for all purposes.

TECHNICAL FIELD

Various embodiments relate to an embolic device, an apparatus for embolizing a target vascular site, and a method of embolizing a target vascular site.

BACKGROUND

Embolization is a minimally invasive procedure to selectively occlude blood vessels by intentionally introducing embolic agents into the blood vessels. Generally, the embolization procedure is carried out by percutaneous insertion of a catheter into the desired blood vessel (artery or vein) under X-ray fluoroscopy guidance. Once in place, an embolic agent is then deployed to stop blood flow by either direct occlusion of the blood vessel or induction of local thrombosis, or both.

Embolization is applied to treat various conditions whereby occlusion of blood vessels is beneficial. For example, such conditions may include but are not limited to traumatic hemorrhage, bleeding from gastrointestinal or respiratory tracts, arteriovenous malformations (AMVs), aneurysm, uterine fibroids, transcatheter arterial chemoembolization (TACE) and selective internal radiation therapy (SIRT) for unresectable liver tumors.

To date liver cancer is the third leading cause of cancer death worldwide and is highly prevalent in Asia. Less than 30% of primary liver cancer patients and less than 10% of metastatic liver cancer patients may be eligible for surgical removal while the remaining patients may only turn to palliative treatments such as TACE and SIRT.

Generally in TACE, the hepatic artery is embolized following delivery of chemotherapeutic agents into the artery. The purpose of the embolization of the hepatic artery is twofold being (i) to prevent the washout of the therapeutic drug at the site of tumor and (ii) to induce tumor ischemia. The desired outcome is to enhance the efficacy of chemotherapy while reducing systemic exposure. In TACE, repeat procedures are common so patency of the hepatic arteries needs to be restored before a subsequent TACE is performed. Therefore, temporary occlusion of the hepatic artery using a biodegradable agent is desirable. In this procedure, Gelfoam, a biodegradable gelatin sponge, is typically used. It may be cut into small pledgets (about 1 mm or larger) and delivered as a particulate embolic agent.

In other instances, occlusion of vessels may be required to divert blood flow or to protect the vascular territory from reflux of toxic materials: For example in SIRT of liver cancers, radio-active particles are delivered into the hepatic artery and the gastroduodenal artery (GDA) is often prophylactically embolized to prevent reflux of the radioactive particles into the stomach and small intestines as the radioactive particles cause radiation ulcers which often lead to devastating gastrointestinal hemorrhages. Currently, solid embolic device in the form of coil may be used Coil-form solid embolic devices are usually made of metals (e.g., stainless steel, platinum or nitinol alloys) and are therefore non-biodegradable. As the reflux prophylaxis is only relevant during delivery of the radioactive particles, permanent occlusion of the GDA is unnecessary and biodegradable embolic may be desirable in such a situation.

Currently, there are limited types of biodegradable embolic devices available. In this regard, Gelfoam may be considered the most widely used biodegradable embolic agent for intravascular embolization. It may be typically resorbed in days to weeks depending on the amount of uses, the degree of fluid saturation and the site of use. However, permanent occlusion may occur by residual organized thrombi or fibrotic change of the vessel. In addition, the occlusion level may be unpredictable because of the irregular shape and variability in size of the Gelfoam. In general, Gelfoam tends to aggregate in vessels more proximally than intended, and significantly small fragments of Gelfoam may migrate into capillary beds. Therefore, it is difficult to perform controlled target embolization using these agents. Occlusin™ 500 Artificial Embolization Device (OCL 500, IMBiotechnologies Ltd., Edmonton (Alberta), Canada) is another biodegradable embolic agent for highly vascularised tumors. The agent consists of biodegradable poly-lactic-co-glycolic acid (PLGA) microspheres coated with type I bovine collagen. Although OCL 500 is manufactured in multiple size ranges, there is a risk of migration of microspheres during the administration process. Yet another type of embolic agent is a biodegradable liquid embolic agent and fibrin glue may currently be the only one available in the market. However, despite its good biocompatibility, the use of fibrin glue is hindered by its fast degradation and need for double-lumen catheterization.

Accordingly, there is a need for a biodegradable embolic device (e.g., a biodegradable embolic foam or plug) that precisely occludes the blood vessel and degrades at a predictable rate, thereby addressing at least the problems above. This aims to facilitate recanalization of the blood vessels and allow embolization procedures to be repeated, especially in liver cancer treatment.

SUMMARY

According to an embodiment, an embolic device for embolizing a target vascular site is provided. The embolic device may include a biodegradable shape memory element having an original shape and a deformed shape. The biodegradable shape memory element in the deformed shape may be in at least one dimension of a smaller size than the biodegradable shape memory element in the original shape. The biodegradable shape memory element may be provided in the deformed shape and configured to resume the original shape in response to an external stimulus being applied to the biodegradable shape memory element in its deformed shape, to embolize the target vascular site and prevent fluid flow through the target vascular site.

According to an embodiment, an apparatus for embolizing a target vascular site is provided. The apparatus may include an embolic device in accordance with various embodiments, and a catheter configured to deliver the embolic device to the target vascular site.

According to an embodiment, a method of embolizing a target vascular site is provided. The method may include providing an embolic device in accordance with various embodiments, inserting a catheter toward the target vascular site, loading the embolic device including the biodegradable shape memory element in the deformed shape into the catheter, and delivering the embolic device to the target vascular site to allow the biodegradable shape memory element in the deformed shape to resume the original shape to embolize the target vascular site.

BRIEF DESCRIPTION OF THE DRAWINGS

In the drawings, like reference characters generally refer to like parts throughout the different views. The drawings are not necessarily to scale, emphasis instead generally being placed upon illustrating the principles of the invention. In the following description, various embodiments of the invention are described with reference to the following drawings, in which.

DETAILED DESCRIPTION

Figure 1A:
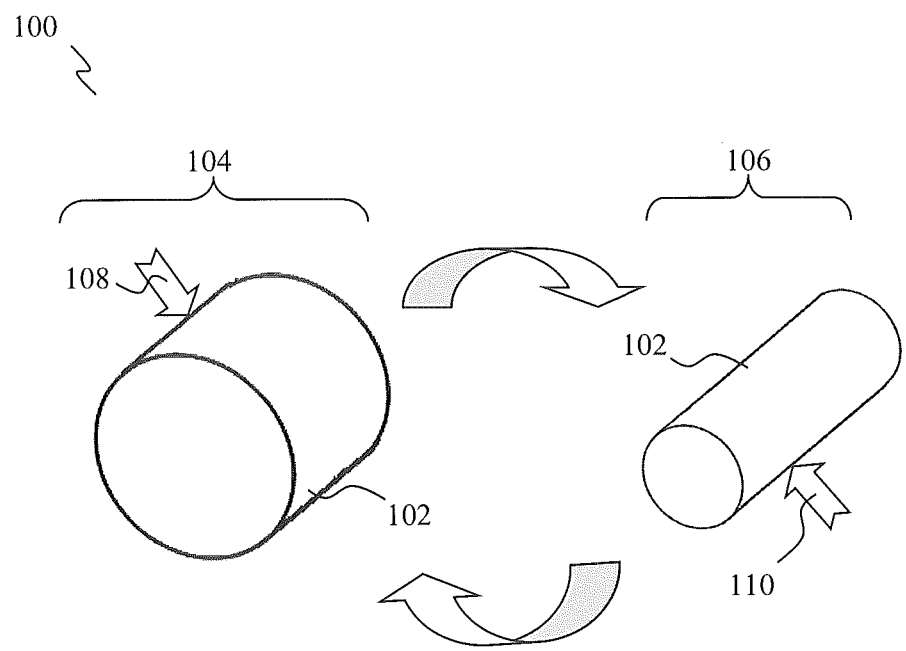
FIG. 1A shows a schematic view of an embolic device for embolizing a target vascular site, according to various embodiments.

The following detailed description refers to the accompanying drawings that show, by way of illustration, specific details and embodiments in which the invention may be practiced. These embodiments are described in sufficient detail to enable those skilled in the art to practice the invention. Other embodiments may be utilized and structural, logical, and electrical changes may be made without departing from the scope of the invention. The various embodiments are not necessarily mutually exclusive, as some embodiments can be combined with one or more other embodiments to form new embodiments.

Embodiments described in the context of one of the methods or devices are analogously valid for the other methods or devices. Similarly, embodiments described in the context of a method are analogously valid for a device, and vice versa.

Features that are described in the context of an embodiment may correspondingly be applicable to the same or similar features in the other embodiments. Features that are described in the context of an embodiment may correspondingly be applicable to the other embodiments, even if not explicitly described in these other embodiments. Furthermore, additions and/or combinations and/or alternatives as described for a feature in the context of an embodiment may correspondingly be applicable to the same or similar feature in the other embodiments.

In the context of various embodiments, the articles "a", "an" and "the" as used with regard to a feature or element include a reference to one or more of the features or elements.

In the context of various embodiments, the phrase "at least substantially" may include "exactly" and a reasonable variance.

In the context of various embodiments, the term "about" or "approximately" as applied to a numeric value encompasses the exact value and a reasonable variance.

As used herein, the term "and/or" includes any and all combinations of one or more of the associated listed items.

As used herein, the phrase of the form of "at least one of A or B" may include A or B or both A and B. Correspondingly, the phrase of the form of "at least one of A or B or C", or including further listed items, may include any and all combinations of one or more of the associated listed items.

Various embodiments may provide biodegradable shape memory polymer embolic devices for temporary endovascular embolization.

Various embodiments may relate to endovascular embolization and more particularly to drug-eluting biodegradable shape memory polymer embolic devices for temporary endovascular embolization.

Various embodiments may provide a biodegradable embolic device for occluding blood vessel. The embolic device may include a biodegradable shape memory polymer (SMP) and a water-responsive material. The biodegradable shape memory polymer may include a copolymer of polylactic acid and polyglycolide. The biodegradable shape memory polymer may include a shape memory polymer foam having an open cell foam structure including a radiopaque marker. The biodegradable shape memory polymer may be customized to degrade in a period of about 216 weeks. The water-responsive material may include water soluble or swellable Materials. The biodegradable embolic device may be incorporated with therapeutic agents for anti-thrombogenic purpose. The release of therapeutic agents may last up to 90 days.

Various embodiments may provide a water activated biodegradable hydrogel composite device for embolization of blood vessel.

Various embodiments may provide a method of occluding a blood vessel using a water-responsive shape memory polymer embolic device. The shape memory polymer may be actuated by a solvent so that the secondary (deformed) shape may resume its primary (original) shape upon external stimulus, e.g., blood.

Various embodiments may provide a method of occluding a blood vessel. The method may include providing a biodegradable embolic device including a biodegradable SMP and a water-responsive material, wherein the biodegradable embolic device has been deformed to a diameter smaller than the inner diameter of a target vessel of a living mammal, inserting the embolic device into the vessel via a catheter, and upon exposure to body fluid, recovering its primary (original) shape and generally conforming to the diameter of the target vessel.

FIG. 1A shows a schematic view of an embolic device 100 for embolizing a target vascular site, according to various embodiments. The embolic device 100 includes a biodegradable shape memory element 102 having an original shape 104 and a deformed shape 106. The biodegradable shape memory element 102 in the deformed shape 106 is in at least one dimension of a smaller size than the biodegradable shape memory element 102 in the original shape 104, and the biodegradable shape memory element 102 is provided in the deformed shape 106 and configured to resume the original shape 104 in response to an external stimulus 110 being applied to the biodegradable shape memory element 102 in its deformed shape 106, to embolize the target vascular site and prevent fluid flow through the target vascular site.

In other words, the embolic device 100 may include a biodegradable shape memory element 102 configured to transition between a original shape 104 and a deformed shape 106, wherein the biodegradable shape memory element 102 in the deformed shape 106 may be in at least one dimension of a smaller size than the biodegradable shape memory element 102 in the original shape 104 such that the biodegradable shape memory element 102 in the deformed shape 106 may be incapable of embolizing the target vascular site to prevent fluid flow through the target vascular site; and wherein the biodegradable shape memory element 102 in its deformed shape 106 may be configured to transit to the original shape 104 in a controlled and predictable manner to embolize the target vascular site and prevent fluid flow through the target vascular site.

In various embodiments, the embolic device 100 may be for temporary embolizing the target vascular site Upon use, the biodegradable shape memory element 102 may be configured to degrade at a predictable rate, e.g., within a period of about 2 weeks to about 16 weeks. Accordingly, the embolic device 100 may be, configured to facilitate recanalization of the target vascular site and subsequently allow for embolization procedures to be repeated. In the repeated embolization procedures, a separate embolic device (e.g., similar to the embolic device 100) may be used for a subsequent embolization of the target vascular site Such repeated embolization procedures may be appropriate for various cancer treatments, e.g., liver cancer treatment.

In various embodiments, the embolic device 100 may be a biodegradable solid embolic device.

In the context of various embodiments, the phrase "target vascular site" may mean a target part of a blood vessel.

In various embodiments, the biodegradable shape memory element 102 may be configured to transit from the original shape 104 to the deformed shape 106 in response to an external stimulus 108 being applied to the biodegradable shape memory element 102 in its original shape 104.

In various embodiments, the biodegradable shape memory element 102 may be configured to transit from the original shape 104 to the deformed shape 106 upon exposure to an external stimulus 108 in form of externally applied pressure optionally at a temperature sufficient to allow the transition of the biodegradable shape memory element 102 from the original shape 104 to the deformed shape 106. In other words, the external stimulus 108 may be in form of externally applied pressure optionally at a temperature sufficient to allow the transition of the biodegradable shape memory element 102 from the original shape 104 to the deformed shape 106 and this temperature may be referred to as a transition temperature. For example, the transition temperature may be in the range of about 10° C. to about 80° C.

For example, the biodegradable shape memory element 102 may be a foam made of a polymer which may be capable of retaining its deformed shape (or compressed state) by warming the polymer above its glass transition temperature, compressing the foam and cooling the foam in the compressed state to retain the foam in the compressed state.

In another embodiment, the biodegradable shape memory element 102 may be a polymer-hydrogel composite which may be capable of retaining its deformed shape by warming the polymer-hydrogel composite above its transition temperature, stretching the polymer-hydrogel composite and cooling the composite in the deformed state to retain the polymer-hydrogel composite in the compressed state.

Alternatively, the original shape 104 may be in the form of a coil having the same or variable (peripheral) diameter. The coil may be heated to its transition temperature and then may be uncoiled to the form of a substantially straight filament having a diameter suitable to fit in the catheter and subsequently may be cooled below its transition temperature.

In various embodiments, the biodegradable shape memory element 102 in its deformed shape 106 may be configured to resume the original shape 104 upon exposure to an external stimulus 110 in form of coming into contact with water or being exposed to an elevated temperature. In an example, the external stimulus 110 may relate to a body fluid, e.g., blood flowing through the target vascular site. In another example, depending on the type of material used for the biodegradable shape memory element 102, the external stimulus 110 may relate to the elevated temperature of the normal body temperature at about 37° C.

In yet another example, the external stimulus 110 for recovering the original shape 104 may be fluid i.e. blood flowing through the target vascular site, or body temperature, or both acting simultaneously. Another stimulus 110 such as external heating pads or inductive heating using alternating magnetic field for suitably modified polymer composition may be used if the activation temperature is higher than the body temperature.

In various embodiments, the biodegradable shape memory element 102 configured to resume the original shape 104 may be of a plug configuration.

In the context of various embodiments, the phrase "resume the original shape" may mean recovery of shape and size to those of the original shape.

In various embodiments, the biodegradable shape memory element 102 in the original shape 104 may have at least one of a different size or a different peripheral (outline) shape to the biodegradable shape memory element 102 in the deformed shape 106.

In various embodiments, the biodegradable shape memory element 102 in the original shape 104 may generally be shaped and sized substantially similarly to the dimensions of the target vascular site. More specifically, the biodegradable shape memory element 102 in the original shape 104 may have a size and a peripheral (outline) shape that is the same or substantially similar to the size and shape defined by the inner walls of the target vascular site.

The biodegradable shape memory element 102 in the deformed shape 106 being in at least one dimension of a smaller size than the biodegradable shape memory element 102 in the original shape 104 may mean that the biodegradable shape memory element 102 may be at least substantially cylindrical and the biodegradable shape memory element 102 in the deformed shape 106 may have a diameter smaller than that of the biodegradable shape memory element 102 in the original shape 104.

In various embodiments, the biodegradable shape memory element 102 in the original shape 104 may be at least substantially cylindrical. The biodegradable shape memory element 102 in the original shape 104 may have a diameter of about 3 mm to about 10 mm. For example, the biodegradable shape memory element 102 in the original shape 104 may have a diameter of about 4 mm to about 10 mm, or about 5 mm to about 10 mm, or about 6 mm to about 10 mm, or about 7 mm to about 10 mm, or about 8 mm to about 10 mm, or about 9 mm to about 10 mm, or about 4 mm to about 9 mm, or about 5 mm to about 9 mm, or about 6 mm to about 9 mm, or about 7 mm to about 9 mm, or about 8 mm to about 9 mm, or about 4 mm to about 8 mm, or about 5 mm to about 8 mm, or about 6 mm to about 8 mm, or about 7 mm to about 8 mm, or about 4 mm to about 7 mm, or about 5 mm to about 7 mm, or about 6 mm to about 7 mm, or about 4 mm to about 6 mm, or about 5 mm to about 6 mm, or about 4 mm to about 5 mm.

In various embodiments, the biodegradable shape memory element 102 in the deformed shape 106 may generally take any shape and/or size as long as the biodegradable shape memory element 102 in the deformed shape 106 may be smaller than the biodegradable shape memory element 102 in the original shape 104 and may be inserted through a catheter for accessing the target vascular site.

For example, the biodegradable shape memory element 102 in the deformed shape 106 may be at least substantially cylindrical. The biodegradable shape memory element 102 in the deformed shape 106 may have a diameter of about 0.3 mm to about 1.0 mm. For example, the biodegradable shape memory element 102 in the deformed shape 106 may have a diameter of about 0.4 mm to about 0.9 mm, or about 0.5 mm to about 0.8 mm, or about 0.6 mm to about 0.7 mm. The biodegradable shape memory element 102 may retain in the deformed shape 106 by crystallization or vitrification of the polymeric chain of the biodegradable shape memory element 102.

The size (or diameter) ratio between the biodegradable shape memory element 102 in the original shape 104 and the biodegradable shape memory element 102 in the deformed shape 106 may be in a range of about 2 to about 25.

In various embodiments, the biodegradable shape memory element 102 configured to resume the original shape 104 may mean that the biodegradable shape memory element 102 may be configured to "remember" its original shape 104 and transit toward the original shape 104, and not to any other shape or irregular shape. For example, if the biodegradable shape memory element 102 in the original shape 104 is cylindrical, the biodegradable shape memory element 102 transited to the deformed shape 106 may be cylindrical and the biodegradable shape memory element 102 resumed to the original shape 104 may also be cylindrical.

The capabilities of the biodegradable shape memory element 102 to transit between the original shape 104 and the deformed shape 106 at a predetermined size ratio and to resume the original shape 104 may mean that the biodegradable shape memory element 102 may be configured to transit to the original shape 104 in a controlled and predictable manner.

In various embodiments, the biodegradable shape memory element 102 may be of a biocompatible material.

In various embodiments, the biodegradable shape memory element 102 may include a biodegradable shape memory polymer (SMP) or copolymer.

In various embodiments, the biodegradable shape memory element may have a foam structure and the deformed shape may be a compressed shape.

In various embodiments, the biodegradable shape memory element 102 may include an open-cell foam structure. In other words, the open-cell foam structure may include gas pockets that are connected with each other.

The mean pore size of the foam structure may be about 0.1 mm, to about 0.5 mm. This may advantageously allow for promoting rapid aspiration of blood fluid into the foam, thereby aiding foam expansion, and for a foam structure with relatively high expansibility.

The biodegradable shape memory element 102 may be in a non-particulate form. For example, the biodegradable shape memory element 102 may be a single whole structure, different from a particulate structure formed by a number of parts (particles) coming together (e.g., adjacent to one another).

The biodegradable shape memory element 102 may be surface-erode or bulk-erode.

In various embodiments, the biodegradable shape memory element 102 may include a polymer material selected from the group consisting of polyesters, polylactide acid, polyglycolide, polycaprolactones, poly(anhydrides), poly(ortho esters), and any mixture or copolymers thereof.

In various embodiments, the copolymer may include poly(D,L-lactide-co-glycolide), poly-3-hydroxybutyrate-co-3-hydroxyvalerate, polylactide-co-poly(glycolide-co-caprolactone), poly(glycol-glycerol-sebacate), poly(lactide-co-p-dioxanone) or poly(lactide-co-ε-caprolactone).

In various embodiments, the embolic device 100 may further include a water-responsive element configured to react upon exposure to water and cause or facilitate the biodegradable shape memory element 102 in the deformed shape 106 to resume the original shape 104.

In an example, the biodegradable shape memory element 102 may be distributed at a core area or as a core, with the water responsive element surrounding or covering at least part of the biodegradable shape memory element 102.

The water-responsive element may retain the biodegradable shape memory element 102 in its deformed shape 106 in the absence of water.

In various embodiments, the water-responsive element may include a hydrogel. For example, the water-responsive element may include a material selected from the group consisting of polyethylene glycol, gelatin hydrogel, cellulose acetate, polyvinyl alcohol, chitosan, and any combination thereof.

The water-responsive element may be made of a water soluble material or a water swellable material.

In an example, the water-responsive element may hold the biodegradable shape memory element 102 in the deformed shape 106 and upon exposure to water (body fluid), the water-responsive element made of a water soluble material may dissolve and thus unable to hold the biodegradable shape memory element 102 in the deformed shape 106. Consequently, the biodegradable shape memory element 102 may resume the original shape 104.

In another example, the water-responsive element may hold the biodegradable shape memory element 102 in the deformed shape 106 and upon exposure to water (body fluid), the water-responsive element made of a water swellable material may swell or expand outwardly and thus prevent the biodegradable shape memory element 102 from retaining in the deformed shape 106. Consequently, the biodegradable shape memory element 102 may resume the original shape 104.

In various embodiments, the biodegradable shape memory element 102 may include a biodegradable shape memory polymer forming a backbone or core structure and the water-responsive element may include a hydrogel applied as a coating to the biodegradable shape memory polymer 102, to form a biodegradable shape memory polymer:hydrogel hybrid.

The hydrogel may coat the biodegradable shape memory polymer and the biodegradable shape memory polymer:hydrogel hybrid may retain in its (compressed) deformed shape and upon contact with water, the hydrogel may swell so that the recovery of shape may occur concurrently. For example, the biodegradable shape memory polymer may include poly(lactic-co-glycolic acid) and the hydrogel applied as the coating may include polyethylene glycol.

In various embodiments, the embolic device 100 may further include a therapeutic agent.

For example, the therapeutic agent may be heparin or heparin-albumin conjugates or hyaluronic acid, for anti-thrombogenic purposes.

The therapeutic agent may be incorporated into the biodegradable shape memory element 102, or the water-responsive element, or both depending of the intended release kinetics. Incorporation of the therapeutic agent may be done by compounding. The therapeutic agent may be eluted up to 90 days to prevent acute and chronic thrombosis.

In various embodiments, the embolic device 100 may further include a radiopaque market configured to provide visibility of at least part of the embolic device 100 under exposure to a radiant energy source.

In various embodiments, the radiopaque marker may be located within the embolic device 100 along its centre axis. In other words, the radiopaque marker may form a radiopaque marker core.

In other embodiments, the radiopaque marker may include a plurality of radiopaque markers dispersed within the embolic device 100.

For example, the radiopaque marker may include barium sulfate, or platinum, or a gold nanoparticle or tantalum or iodine or bismuth oxychloride or bismuth trioxide or bismuth subcarbonate or a radiocontrast medium. The radiant energy source may include an X-ray source. The radiopaque marker may be configured to provide visibility of the at least part of the embolic device 100 under X-ray fluoroscopy. The radiopaque marker may be configured to provide proper placement of the embolic device 100 at the target vascular site.

Figure 1B:
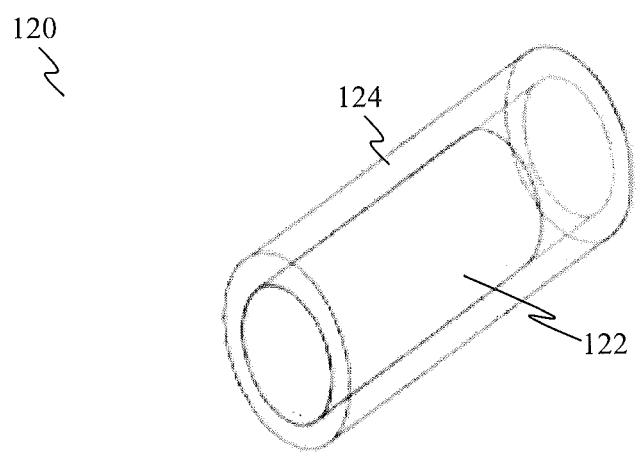
FIG. 1B shows a schematic view of an apparatus for embolizing a target vascular site, according to various embodiments.

FIG. 1B shows a schematic view of an apparatus 120 for embolizing a target vascular site, according to various embodiments. The apparatus 120 includes an embolic device 122, and a catheter 124 configured to deliver the embolic device 122 to the target vascular site.

The embolic device 122 may include the same or like elements or components as those of the embolic device 100 of FIG. 1A, and as such, the same numerals are assigned and the like elements may be as described in the context of the biodegradable shape memory element 102 and the deformed shape 106 of FIG. 1A, and therefore the corresponding descriptions are omitted.

In FIG. 1B, the biodegradable shape memory element 102 of the embolic device 122 is in the deformed shape 106, and the embolic device 122 is loaded into the catheter 124.

In various embodiments, the biodegradable shape memory element 102 of the embolic device 122 in the deformed shape 106 may be adapted to pass through the catheter 124 to allow the embolic device 122 to exit a distal end of the catheter 124 to the target vascular site.

In various embodiments, the apparatus 120 may further include an element configured to deliver the embolic device 122 from the catheter 124 to the target vascular site. In other words, the element may be inserted through the catheter 124 at one end to reach and push the embolic device 122 to exit the distal end of the catheter 124 to the target vascular site.

The apparatus 120 may further include a radiant energy source (as described herein) configured to provide a radiant energy (e.g., X-ray) onto a radiopaque marker (as described herein). The apparatus 120 may further include a detector configured to detect the radiated radiopaque marker and allow the embolic device 122 at the target vascular site to be visualized.

Figure 1C:
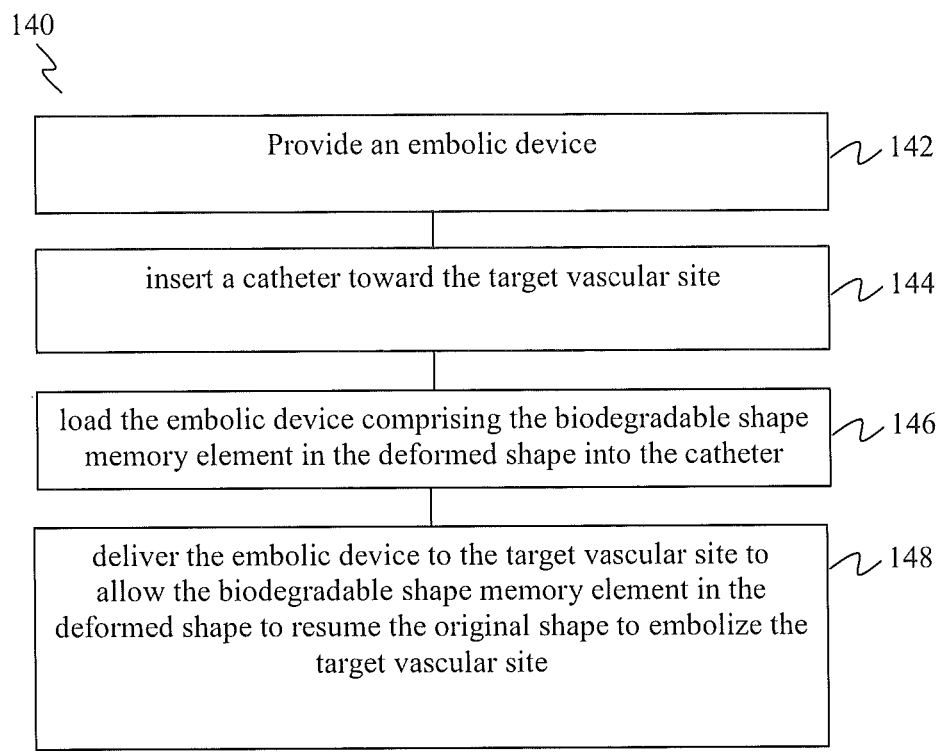
FIG. 1C shows a flow chart illustrating a method of embolizing a target vascular site, according to various embodiments.

FIG. 1C shows a flow chart illustrating a method of embolizing a target vascular site 140, according to various embodiments. At 142, an embolic device in accordance with various embodiments is provided. At 144, a catheter is inserted toward the target vascular site. At 146, the embolic device including the biodegradable shape memory element in the deformed shape is loaded into the catheter. At 148, the embolic device is delivered to the target vascular site to allow the biodegradable shape memory element in the deformed shape to resume the original shape to embolize the target vascular site.

The biodegradable shape memory element resumed to the original shape at the target vascular site may prevent fluid flow through the target vascular site.

The embolic device may include the same or like elements or components as those of the embolic device 100 of FIG. 1A or the embolic device 122 of FIG. 1B, and as such, the like elements may be as described in the context of the biodegradable shape memory element 102, the deformed shape 106, the original shape 104, the external stimulus 110 of FIG. 1A and the catheter 124 of FIG. 1B, and therefore the corresponding descriptions are omitted here.

In various embodiments, delivering the embolic device to the target vascular site 148 may include delivering the embolic device from the catheter to the target vascular site via an element.

In various embodiments, the method 140 may further include prior to loading the embolic device into the catheter 146, exposing the biodegradable shape memory element of the embolic device to an external stimulus in form of externally applied pressure optionally at a temperature sufficient to allow the transition of the biodegradable shape memory element from the original shape to the deformed shape.

While the method described above is illustrated and described as a series of steps or events, it will be appreciated that any ordering of at least some steps or events are not to be interpreted in a limiting sense. For example, some steps may occur in different orders and/or concurrently with other steps or events apart from those illustrated and/or described herein. In addition, not all illustrated steps may be required to implement one or more aspects or embodiments described herein. Also, one or more of the steps depicted herein may be carried out in one or more separate acts and/or phases.

Various exemplary embodiments will now be described below.

Figure 2:
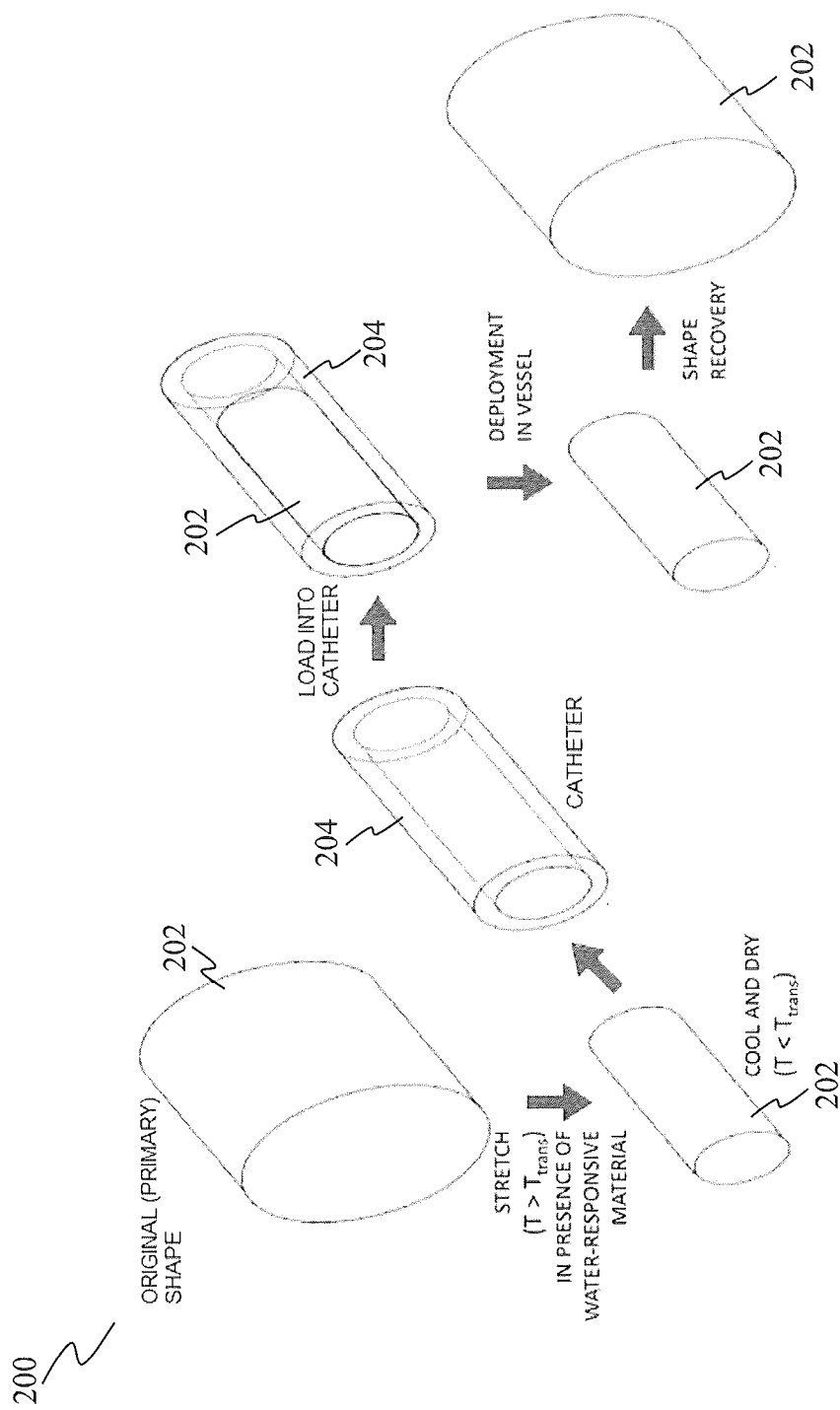
FIG. 2 shows a schematic diagram illustrating an example of a biodegradable embolic device for occluding blood vessel and a process for occluding blood vessel, according to various embodiments.

FIG. 2 shows a schematic diagram 200 illustrating an example of a biodegradable embolic device 202 for occluding a blood vessel and a process for occluding a blood vessel.

For example, the embolic device 202 may be described in the context of the embolic device 100 of FIG. 1A, and elements of the embolic device 202 may also be described in the context of like elements of the embolic device 100 of FIG. 1A.

The embolic device 202 may include a biodegradable shape memory polymer (SMP) and a water responsive material. The biodegradable SMP material body may be heated above its transition temperature (T) and deformed from its primary (original) shape to a secondary (deformed) shape having a diameter smaller than the inner diameter of a target vessel for implantation in the presence of a solution of water-responsive material. Once the SMP material body has been deformed as desired, it may be held in the deformed shape followed by drying and cooling to a temperature below its transition temperature, so that the SMP material body may retain the deformed shape by virtue of the crystallization or vitrification of the polymeric chains.

The deformed embolic device 202 may then be loaded into a catheter 204 and delivered endovascularly to the site or blood vessel (not shown in FIG. 2) for embolization via the catheter 204. Once the catheter 204 is positioned near the embolization site, the device 202 may be deployed into the blood vessel. Upon exposure to body fluid (e.g., blood in the blood vessel), the water-responsive material of the embolic device 202 may either dissolve or swell. As a result, the rigid SMP material body in the deformed configuration (shape) may become soft and its shape may start to resume its primary (original) shape, resulting in the occlusion of the blood vessel.

The embolic device 202 in its primary (original) shape may be of a size and shape which may enable fitting within the blood vessel, e.g., fitting snugly against the wall of the blood vessel. The embolic device 202 in its primary (original) shape may have a diameter of about 3-7 millimeters. The deformed or compressed embolic device 202 may have a diameter of about 0.3-1 millimeter for micro-catheter deployment.

In another example, the embolic device 202 may include a biodegradable SMP. The SMP may be fabricated into foam by a variety of techniques including gas foaming, porogens leaching, solvent blowing, freeze drying process, supercritical $CO_2$ assisted foaming or any combination of the above techniques. The SMP foam may be an open cell foam structure with a mean pore size in the range of about 0.1 to 0.5 millimeters. Such a pore size may be advantageous for the embolic device 202 as (i) rapid aspiration of blood fluid into the foam, aiding foam expansion may be promoted, and (ii) making of foam structure with high expansibility may be allowed. The expansion ratios of the foams may be in the range of 2 to 25. The SMP may be fabricated into the plug configuration via techniques including solvent casting, extrusion, electrospinning, injection moulding, and any combination of these techniques.

SMP foams may be made of any biodegradable polymeric material exhibiting shape memory effect and suitable for use in the application described herein. The biodegradable polymeric materials may be surface-erode or bulk-erode. This may include, but is not limited to, polyesters, polylactide acid, polyglycolide, polycaprolactones, poly (anhydrides), poly (ortho esters) and copolymers and any combination thereof. The SMP composition having the following properties may be desirable: (i) the transition temperature being in the range of 10 to 45° C., and (ii) the polymer being biocompatible and biodegradable over a controlled period of time, e.g., about 2 to 10 weeks. The biodegradable SMP foam may include a copolymer. The copolymer may include a poly (D,L-lactide-co-glycolide). The water-responsive material for use in the exemplary embodiments described herein may include water soluble or swellable polymers. This may include, but is not limited to, polyethylene glycol, gelatin hydrogel, cellulose acetate, polyvinyl alcohol, chitosan, or any combination thereof.

Figure 3A:
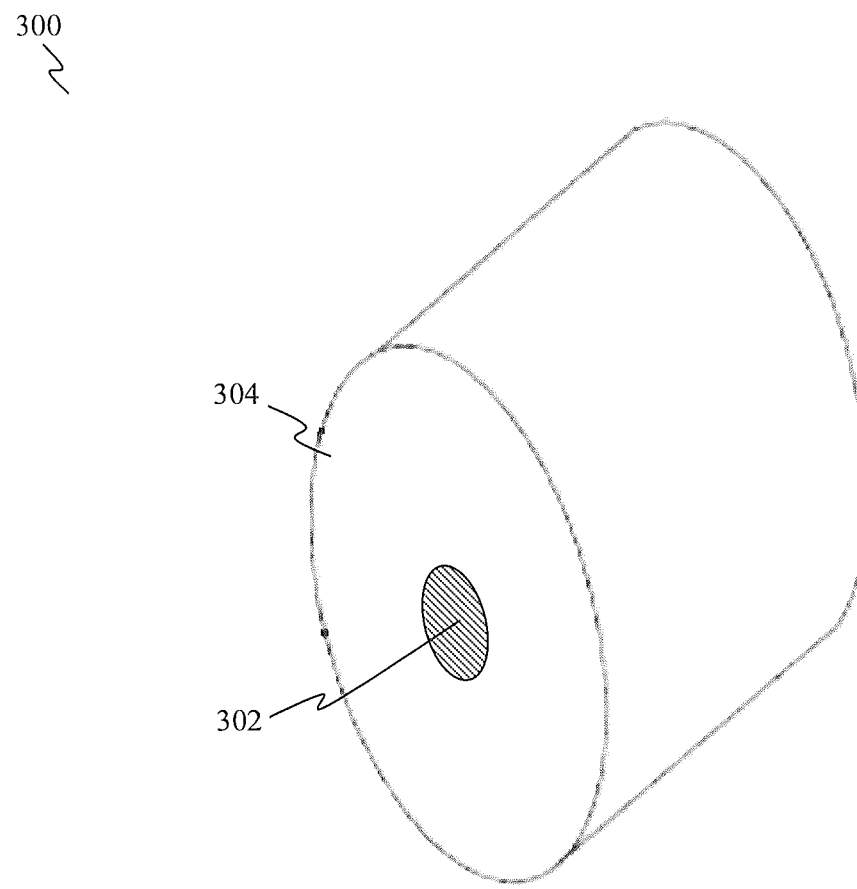
FIG. 3A shows a schematic view of an embolic device with a radiopaque marker core, according to various embodiments.
Figure 3B:
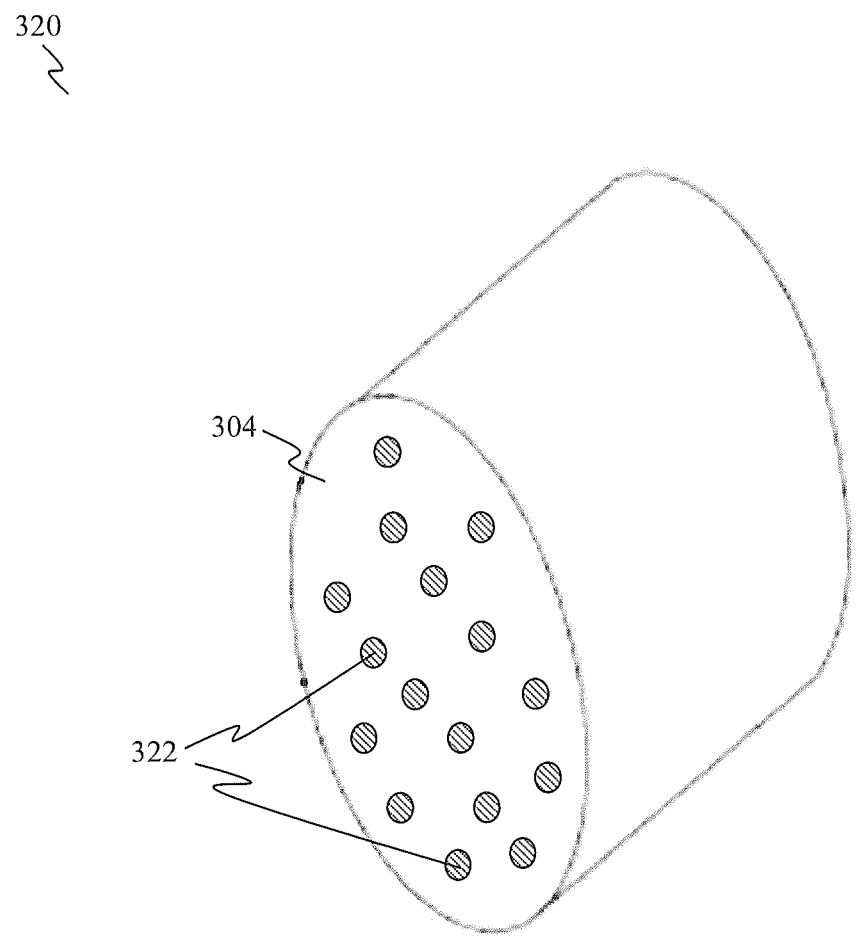
FIG. 3B shows a schematic view of an embolic device with distributed radiopaque markers, according to various embodiments.

The biodegradable embolic device (e.g., the embolic device 202) including the biodegradable SMP and the water-responsive material may include a radiopaque marker such as barium sulfate, gold nanoparticles, platinum, and the like. The purpose of the radiopaque marker may be to provide visibility under X-ray fluoroscopy for proper placement of device. The radiopaque marker may be distributed within the embolic device in different manners as shown in FIGS. 3A and 3B. In FIG. 3A, the embolic device 300 may includes a radiopaque marker core 302, which is embedded by the biodegradable SMP foam 304. In the schematic view 320 of FIG. 3B, the radiopaque markers 322 may distributed, e.g., evenly, within the biodegradable SMP foam 304. The weight percentage of the radiopaque marker 322 may be in the range of about 5% to about 50%.

The biodegradable SMP foam 304 may be described in the context of the biodegradable shape memory element 102 of FIG. 1.

A biodegradable embolic device in accordance with various embodiments may have advantages over conventional devices of being capable of catheter delivery, being easily and accurately positioned, and having rapid and controlled expansion. Additionally, being a foam or plug, there may be a higher degree of occlusion as compared to a metallic coil, which may only embolize vessels partially thus still allowing blood flow through unembolized parts. As coil embolization may typically depend on the ability of a patient to form thrombus, coagulopathic states such as abnormal clotting factors may hinder complete vessel occlusion and time to occlusion may also depend on type of coils used and the patients' condition. Other complications of coil embolization may include vessel rupture due to large mismatch between the mechanical properties of the coil and the vascular wall.

The embolic device in accordance with various embodiments may be programmed and controllably expanded to completely occlude vessels of various sizes by mechanical occlusion. Furthermore, the modulus of the SMP may be accurately controlled so that it may match the mechanical properties of the vascular wall such that the expansion forces may be low, reducing injuries to areas of the vascular lumen. Due to the biodegradability of the embolic devices in accordance with various embodiments, recanalization of the vessels may be facilitated and embolization procedures may be allowed to be repeated in cancer treatment like TACE and SIRT.

A number of tests may be carried out to demonstrate the concept (working principles) of the SMP.

Figure 4:
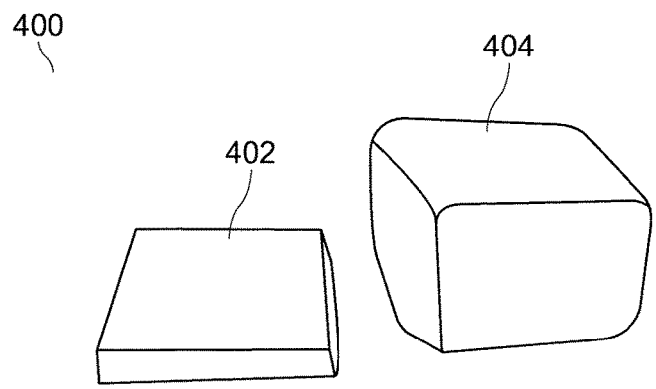
FIG. 4 shows an image of polyurethane (PU) shape memory polymer foams.

For example, as shown in an image 400 of FIG. 4, a piece of polyurethane (PU) shape memory polymer foam 402 is compressed to 95% (left). Upon heating to 37° C., the foam 404 may be shown to be able to fully return to its original shape (right). The expansion ratio may be about 2000%.

Figure 5:
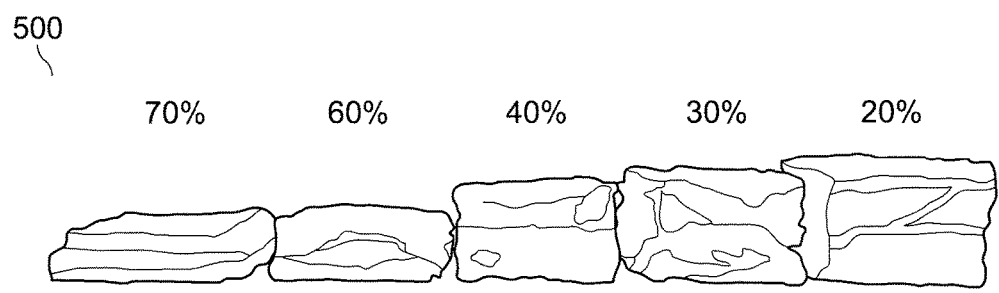
FIG. 5 shows an image of water-responsive shape memory hybrids.

The concept of a water-responsive shape memory hybrid may be demonstrated, as shown in an image 500 of FIG. 5, in which polyethylene glycol (PEG), a water-dissolvable, biocompatible polymer, may be used to hold the compressed polymeric sponge in shape. Without optimization of processing parameters, in the case of 70% compression, the expansion ratio may be about 300%.

Figure 6A:
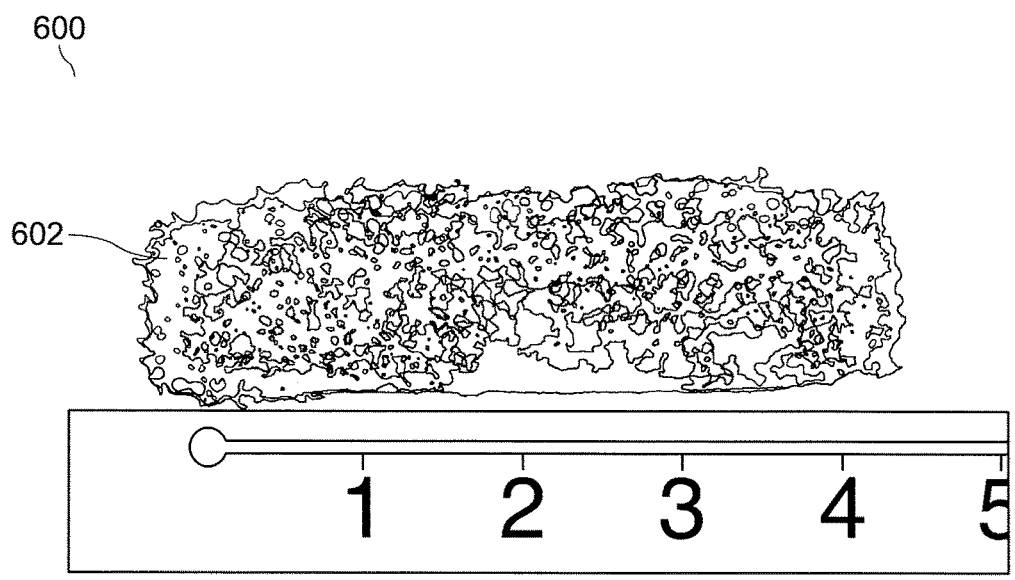
FIGS. 6A to 6D show images demonstrating the concept of a water-responsive plug.
Figure 6B:
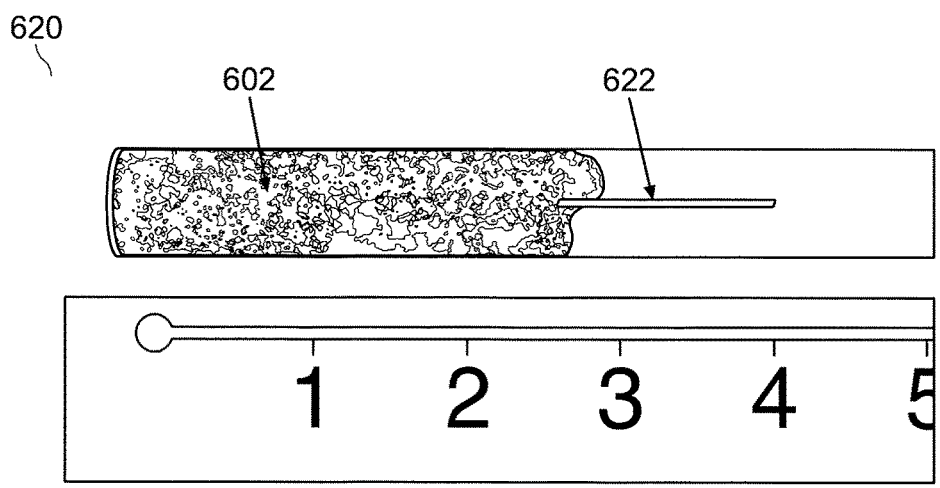
Figure 6C:
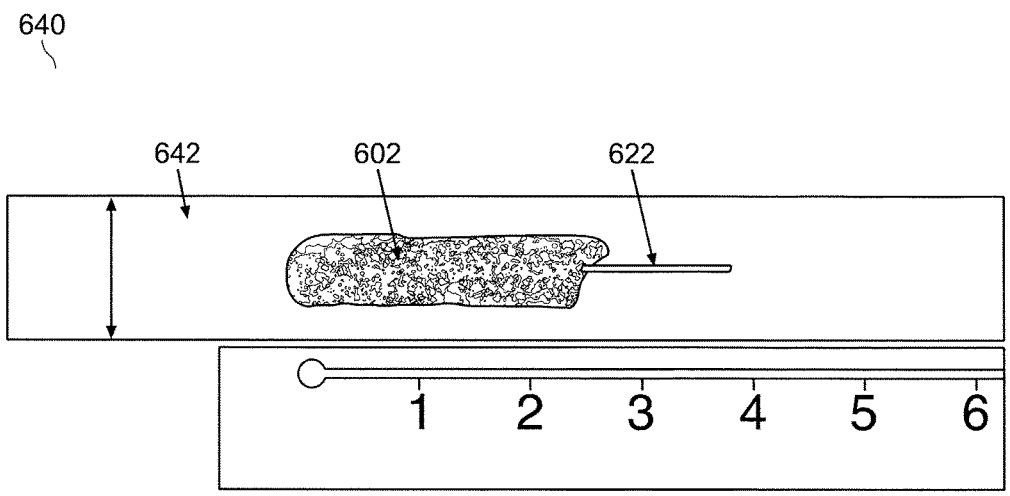
Figure 6D:
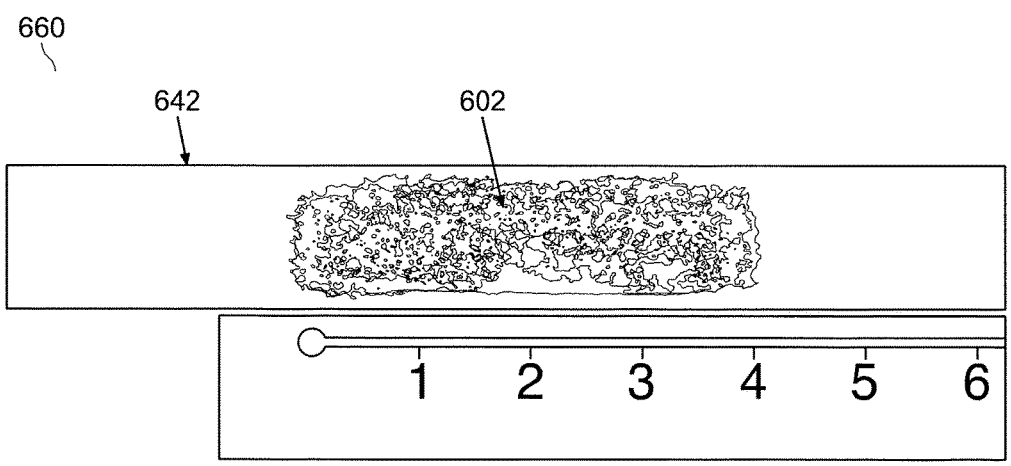

FIGS. 6A to 6D show images 600, 620, 640, 660 demonstrating the concept of a water-responsive plug. In FIG. 6A, a piece of polymeric elastic sponge or plug 602, is compressed, held in the compact shape using PEG and then placed in a plastic tube 622 (FIG. 6B), which represents a catheter. In the next step (FIG. 6C), the plug 602 may be delivered to the required position along a big tube 642 and the polymeric elastic sponge 602 may then be released from the plastic tube 622. After the dissolving of PEG in water, the polymeric elastic sponge 602 may expand and thus block the big tube 642, which may represent a blood vessel (FIG. 6D).

Figure 7:
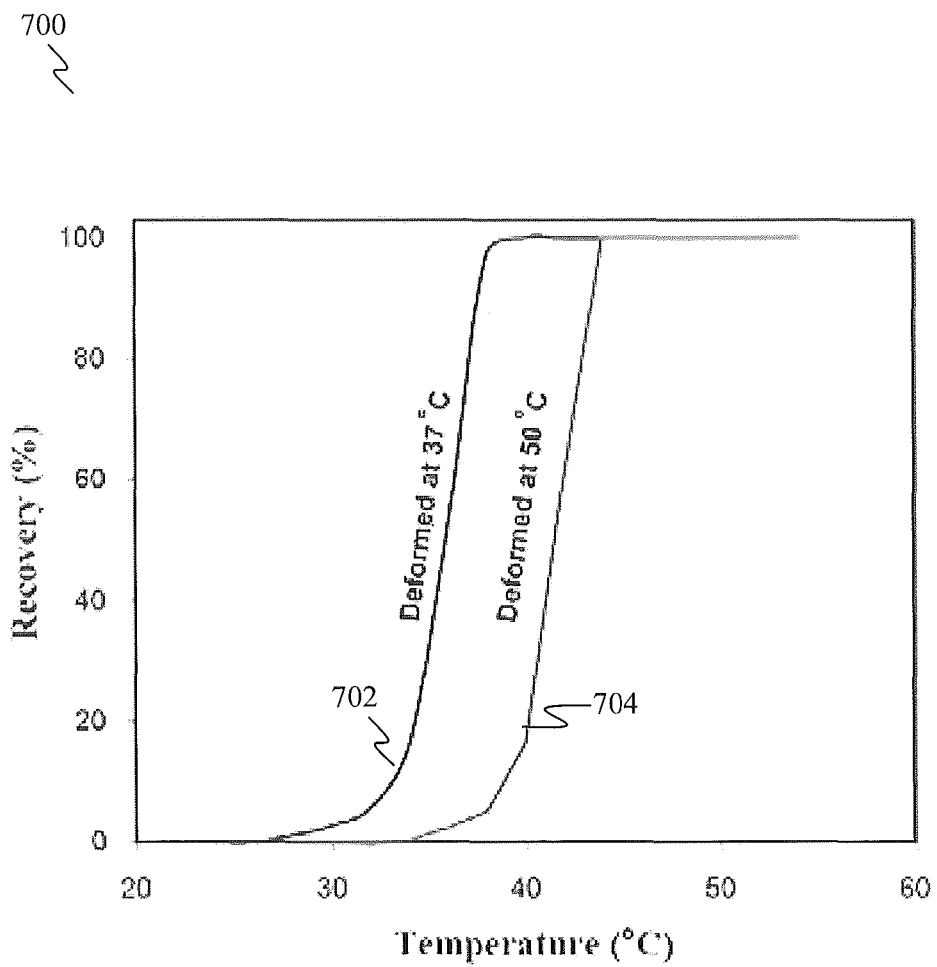
FIG. 7 shows a plot illustrating the recovery ratio of poly(DL-lactide-co-glycolide) (P(DL)GA) (500% pre-stretched) upon gradually heating.

FIG. 7 shows a plot illustrating the recovery ratio of poly(DL-lactide-co-glycolide) (P(DL)GA), which is biodegradable, upon heating. The sample may be pre-stretched to 500% and the recovery temperature may be at about normal body temperature and may be adjustable by using different stretching temperature. Plotline 702 refers to the sample deformed at 37° C., while plotline 704 refers to the sample deformed at 50° C.

The tests described in FIGS. 4 to 7 may demonstrate the concepts of (i) the feasibility to deploy an elastic plug by means of thermo/water-responsive shape memory effect; and (ii) the feasibility to achieve significant shape recovery ratio in biodegradable polymers by means of optimizing the processing parameters in pre-distortion.

In another example, water induced shape memory effect and swelling of a hydrogel may be responsible for the deployment of an embolic device inside a blood vessel, as shown in the schematic views 800, 820, 840, 860 of FIGS. 8A to 8D. Hydrogel may be coated on P(DL)GA, which may serve as the backbone for enhanced performance.

In an exemplary process, a P(DL)GA strand 802 may be coated with a hydrogel 804 using a UV crosslinking method. After drying the gel 804, the embolic device 806 with the P(DL)GA 802 in the core and the dry hydrogel 804 coating on surface may be obtained. For example, the embolic device 806 may be described in the context of the embolic device 100 of FIG. 1A, or the embolic device 122 of FIG. 1B.

In various embodiments, the radiopaque marker may be located within the hydrogel 804. For example, the radiopaque marker may include barium sulfate, or platinum, or a gold nanoparticle or tantalum or iodine or bismuth oxychloride or bismuth trioxide or bismuth subcarbonate or a radiocontrast medium.

A temporary shape of the device 806 (actual dimensions used for deployment) may be programmed by heating the device 806 at about the transition temperature of both the P(DL)GA 802 and the hydrogel 804, and then stretching it (about four times the original length) and quenching it to room temperature so as to obtain the device 806 with the required diameter for deployment.

Figure 8A:
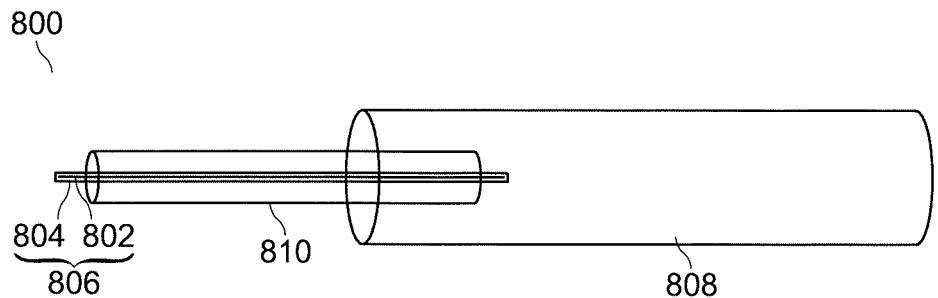
FIGS. 8A to 8D show schematic views of an embolic device and its mechanism of embolization, according to various embodiments.
Figure 8B:
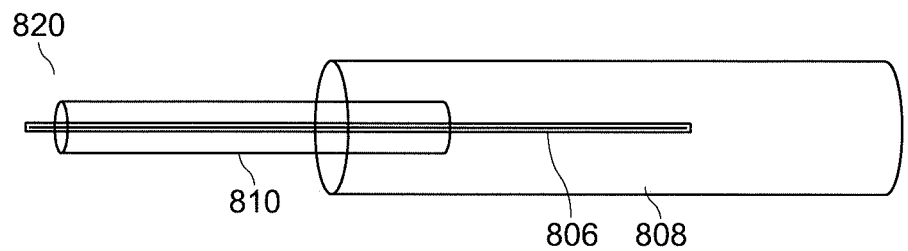
Figure 8C:
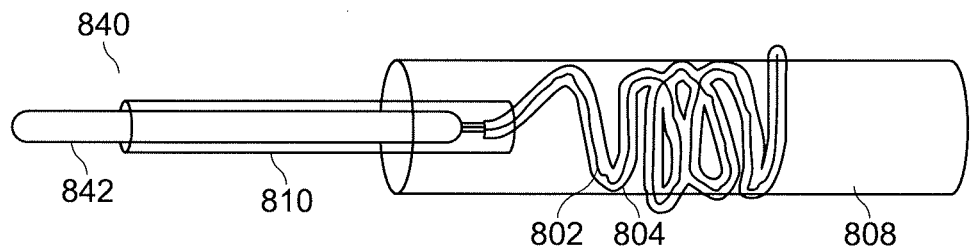
Figure 8D:
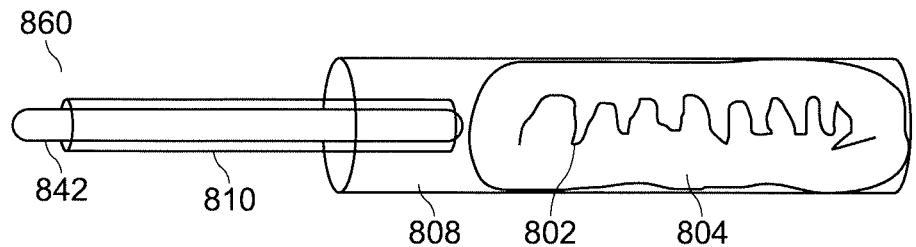

When such a device (e.g., the embolic device 806) is deployed in a blood vessel 808 through a catheter 810 (FIGS. 8A and 8B), the embolic device 806 may come in contact with blood fluid and may start recovering to its permanent (original) shape of a reduced length. Recovery may be activated by the fluid medium (e.g., blood). A pushing wire 842 (e.g., the element for delivering the embolic device from the catheter to the target vascular site as described herein in accordance with various embodiments) may pass through the catheter 810 and may push the embolic device 806 at one end to deliver the embolic device 806 to the blood vessel 808 (FIG. 8C). The hydrogel 804 coating may become soft and may start to return the permanent (original) shape. As the core 802 may still remain hard, the device. 806 may start to buckle and thus may form a random or regular coiled shape (FIG. 8C). Swelling of the gel 804 may start concurrently with the recovery of the shape, so maximum occlusion volume may be achieved within a couple of minutes (FIG. 8D). This device 806 may work based on the buckling phenomenon in water activated shape memory effect and the swelling of the hydrogel 804. Both the hydrogel 804 (polyethylene glycol (PEG) may be used) and the P(DL)GA 802 may be biodegradable.

While the invention has been particularly shown and described with reference to specific embodiments, it should be understood by those skilled in the art that various changes in form and detail may be made therein without departing from the spirit and scope of the invention as defined by the appended claims. The scope of the invention is thus indicated by the appended claims and all changes which come within the meaning and range of equivalency of the claims are therefore intended to be embraced.

The invention claimed is:

1. An embolic device for embolizing a target vascular site, the embolic device comprising:
a straight core which serves as the backbone of the embolic device; and
a water-responsive element having an original shape and a deformed shape, the water-responsive element being coated on the straight core in a manner such that the original shape of the water-responsive element follows the straight core,
wherein the straight core and the water-responsive element are stretched to lengthen into a temporary shape for deployment,
wherein, in the temporary shape for deployment, the water-responsive element is in the deformed shape which is also straight, the water-responsive element in the deformed shape having a cross-sectional diameter of a smaller size than an original cross-sectional diameter of the water-responsive element in the original shape, and the water-responsive element in the deformed shape having a length longer than an original length of the water-responsive element in the original shape,
wherein the straight core and the water-responsive element are provided in the temporary shape,
wherein the water-responsive element is configured to resume the original shape in response to an external stimulus in form of coming into contact with water being applied to the water-responsive element in its deformed shape, and
wherein, when the water-responsive element starts to return to the original shape upon coming into contact with water, the straight core still remain in a stretched and lengthen state, which causes the embolic device to buckle and form a random or regular shape to embolize the target vascular site and prevent fluid flow through the target vascular site.

2. The embolic device of claim 1, wherein the straight core comprises a biodegradable shape memory element, and the biodegradable shape memory element is a biodegradable shape memory polymer or copolymer.

3. The embolic device of claim 2, wherein the biodegradable shape memory element comprises a polymer material selected from the group consisting of polyesters, polylactide acid, polyglycolide, polycaprolactones, poly(anhydrides), poly(ortho esters), and any mixture or copolymers thereof.

4. The embolic device of claim 2, wherein the copolymer comprises poly(D,L-lactide-co-glycolide).

5. The embolic device of claim 1, wherein the water-responsive element comprises a hydrogel.

6. The embolic device of claim 5, wherein the water-responsive element comprises a material selected from the group consisting of polyethylene glycol, gelatin hydrogel, cellulose acetate, polyvinyl alcohol, chitosan, and any combination thereof.

7. The embolic device of claim 1, further comprising a therapeutic agent.

8. The embolic device of claim 1, further comprising a radiopaque marker configured to provide visibility of at least part of the embolic device under exposure to a radiant energy source.

9. An apparatus for embolizing a target vascular site, the apparatus comprising:
   an embolic device of claim 1; and
   a catheter configured to deliver the embolic device to the target vascular site.

10. The apparatus of claim 9, wherein the water-responsive element of the embolic device in the deformed shape is adapted to pass through the catheter to allow the embolic device to exit a distal end of the catheter to the target vascular site.

11. The apparatus of claim 9, further comprising an element configured to deliver the embolic device from the catheter to the target vascular site.

12. A method of embolizing a target vascular site, the method comprising:
   providing an embolic device of claim 1;
   inserting a catheter toward the target vascular site;
   loading the embolic device comprising the water-responsive element in the deformed shape into the catheter; and
   delivering the embolic device to the target vascular site to allow the water-responsive element in the deformed shape to resume the original shape to embolize the target vascular site.

\* \* \* \* \*